United States Patent [19]
Gylys et al.

[11] Patent Number: 5,382,592
[45] Date of Patent: Jan. 17, 1995

[54] ANTIMIGRAINE CYCLOBUTENEDIONE DERIVATIVES OF TRYPTAMINES

[75] Inventors: Jonas A. Gylys, Southington, Conn.; Edward H. Ruediger, Quebec, Canada; David W. Smith, Madison, Conn.; Carola Solomon, Quebec, Canada; Joseph P. Yevich, Southington, Conn.

[73] Assignee: Bristol-Myers Squibb Company, New York, N.Y.

[21] Appl. No.: 122,112

[22] Filed: Sep. 16, 1993

[51] Int. Cl.⁶ ................ A61K 31/40; C07D 209/16
[52] U.S. Cl. ............................. 514/415; 548/504
[58] Field of Search ...................... 514/415; 548/504

[56] References Cited
FOREIGN PATENT DOCUMENTS

| | | |
|---|---|---|
| 0501568A1 | 2/1992 | European Pat. Off. |
| 2124210B | 2/1984 | United Kingdom |
| 2162522A | 2/1986 | United Kingdom |

*Primary Examiner*—Mary C. Lee
*Assistant Examiner*—Jacqueline Haley
*Attorney, Agent, or Firm*—Richard P. Ryan

[57] ABSTRACT

A series of serotonergic 5-cyclobutenedionylamino-substituted tryptamine derivatives of Formula I is disclosed for use in the alleviation of vascular headaches.

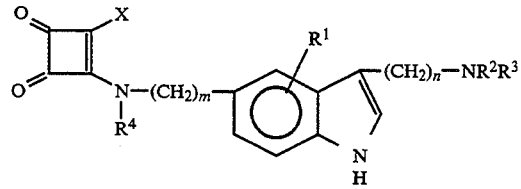

The formula I substituents, as further defined in the specification, are: $R^1$ is hydrogen, halogen, and alkyl; $R^2$ and $R^3$ can be hydrogen or alkyl; $R^4$ is hydrogen, alkyl, acyl or alkylsulfonyl; m is 0 to 3 and n is 1 to 5; and X is amino, alkoxy, hydrogen, alkyl, aryl or alkylaryl.

6 Claims, No Drawings

ANTIMIGRAINE CYCLOBUTENEDIONE DERIVATIVES OF TRYPTAMINES

BACKGROUND OF THE INVENTION

This invention generally pertains to heterocyclic carbon compounds having drug and bio-affecting properties and to their preparation and use. In particular the invention is concerned with cyclobutenedione-substituted tryptamine derivatives. These compounds possess a unique serotonergic profile that renders them useful in treatment of vascular headaches such as migraine or cluster type.

Dowie, et al. disclosed a series of 3-alkylaminoindole derivatives as being potentially useful for the treatment of migraine in a published patent application, GB 2,124,210. One member of this series of compounds was specifically claimed in a later patent application of Oxford, GB 2,162,522, published Feb. 5, 1986. This particular compound is known in the literature as sumatriptan(i).

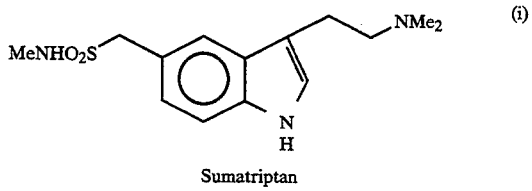

Sumatriptan

A series of substituted cyclic sulfamidoindole derivatives have been disclosed in EP 0501568A as being potentially usefully in treating migraine and associated conditions. One of the compounds specifically claimed is formula (ii).

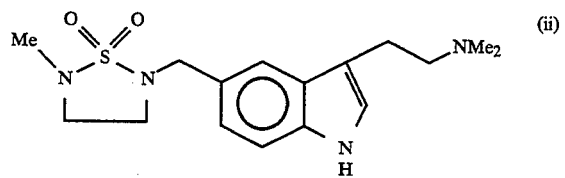

Migraine is a member of a broader class of headache that also comprises cluster headaches and other headaches believed to have a vascular implication in their etiology. These headaches are often classified as vascular headaches. For a current summary of headache and its treatment see: Chapter 13: "Drugs Used to Treat Migraine and Other Headaches" in *Drug Evaluations*, 6th *Edn.*, 1986, pages 239-253 American Medical Association, W. B. Saunders Co., Philadelphia, Pa.

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patient consultation with a physician due to pain severity which is often incapacitating.

Although there is no universally accepted classification system for headache, vascular headache, for the purposes of the present invention, refers mainly to migraine and cluster headaches. Migraine includes the common or classical type as well as migraine variants which would be familiar to one skilled in the art. Other subtypes such as toxic vascular and hypertensive headaches, chronic paroxysmal hemicrania, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

Drugs most commonly used in treatment of headache fall into the following groups:
Ergot Alkaloids,
Beta-blocking Agents,
Calcium Channel Blocking Agents,
Antidepressants, and
Mixtures of these.

Management of recurring vascular headache is complicated by the lack of a single therapy which is effective in all patients with the same headache type and by the need to select either an abortive or prophylactic method of treatment for these headaches. Further complication involves the current use of drugs that cause dependence with extended use, such as ergotamine. Another important consideration for the present invention is that the more effective antimigraine agents in current use, e.g. the ergots, and methysergide, produce severe use-limiting side-effects with long term usage.

Thus there is a need for a safe and effective drug for the treatment of migraine and related disorders which can be used either prophylactically or to alleviate an established headache.

The objectives of the present invention relate to the use of novel cyclobutenedione-substituted tryptamines to provide treatment of vascular headaches, particularly migraine and cluster-types; to processes for their preparation; and to their pharmaceutical compositions and medical usage.

SUMMARY AND DETAILED DESCRIPTION OF THE INVENTION

The method of the present invention is intended for the alleviation of vascular or vascular-related headache of which migraine and cluster are the best known specific examples. The method essentially involves administration of a cyclobutenedione-substituted tryptamine derivative or a pharmaceutically acceptable salt and/or solvate thereof, to a human in need of such treatment. For use in the instant method, oral and transnasal administration of pharmaceutical compositions containing the subject antimigraine agents are preferred.

In a broad aspect, the present invention is concerned with cyclobutenedione derivatives of tryptamine having useful antimigraine serotonergic properties and characterized by Formula I.

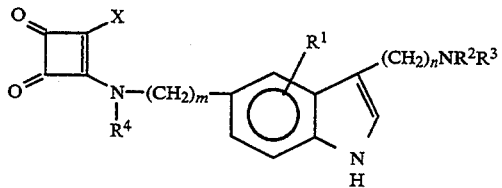

In Formula I, $R^1$ is a substituent selected from hydrogen, halogen and lower alkyl.

$R^2$ and $R^3$ are independently selected from hydrogen and lower alkyl.

$R^4$ is selected from hydrogen, lower alkyl, lower acyl, and lower alkylsulfonyl.

The symbol m is the integers 1 to 3 or zero while the symbol n can be the integers 1 to 5. In preferred compounds, m is zero and n is 2.

X is selected from —$NR^2R^3$; —$OR^2$; and $R^5$, with $R^5$ being hydrogen, lower alkyl, cycloalkyl, aryl, or aryl-lower alkyl.

Additionally, compounds of Formula I also encompass all pharmaceutically acceptable acid addition salts and/or solvates thereof. The present invention is also considered to include stereoisomers as well as optical isomers e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art.

The term "lower alkyl" refers to both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2 methylpropyl. The term "lower acyl" denotes an acyl group containing from 1 to 4 carbons, e.g. a formyl group, a butyryl group, etc. 37 Cycloalkyl" refers to cyclopentyl, cyclohexyl or cycloheptyl groups and "aryl-lower alkyl" refers to phenalkyl groups having alkyl links of from 1 to 4 carbons.

The pharmaceutically acceptable acid addition salts of the invention are those in which the counterion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and others.

Serotonin has been linked to the pathophysiology of migraine by accumulating evidence including increased excretion of serotonin metabolites following a migraine attack and a reduction in the serotonin content of blood platelets during the migraine headache. This latter effect appears to be specific for migraine and not a result of pain or stress. (Anthony, et al., "Plasma serotonin in migraine and stress", *Arch. Neurol.* 1967, 16: 544–552).

More importantly, intramuscular injection of reserpine lowers plasma serotonin and induces a typical migraine-type headache in migraine sufferers. This induced headache can be alleviated by slow I.V. injection of serotonin creatinine sulfate. (Kimball, et al., "Effect of serotonin in migraine patients", *Neurology N.Y.*, 1960, 10: 107–111).

Although serotonin has been shown to be effective in treating migraine attacks, its use in migraine is precluded by its side-effects such as restlessness, nausea, faintness, hyperpnea, facial flushing and parasthesias. (Lance, et al., "The control of cranial arteries by humoral mechanisms and its relation to the migraine syndrome", *Headache*, 1967 7: 93–102) For this reason more specific serotonin agents, which would treat the migraine without all of the other actions, are potentially useful antimigraine medicaments. Accumulating findings have led to the perception that compounds with selectivity for the 5-$HT_{1D}$ sub-type of serotonin receptors would be clinically efficacious in the treatment of migraine. In this regard the compounds of the instant invention demonstrate potent affinity and agonist activity at the 5-$HT_{1D}$ site. Formula I compounds of interest have potencies wherein $IC_{50}$ values of these compounds are less than 100 nmolar. Preferred compounds have $IC_{50}$ values below 10 nmolar.

Determination of 5-$HT_{1D}$ binding properties was accomplished employing methodology such as that described by Heuring and Peroutka, *J. Neurosci.*, 7 (3), 1987, 894–903; with only minor modifications. In vitro $IC_{50}$ (nM) test values were determined for the compounds of this invention employing tritiated serotonin.

In addition to the 5-$HT_{1D}$ binding test data, ability of the compounds of this invention to elicit contraction in a canine saphenous vein model further indicates usefulness in treating vascular headaches. Another aspect then of the instant invention provides a method for treating a migraine sufferer which comprises systemic administration to the sufferer of a therapeutically effective amount of a compound of Formula I or a pharmaceutically acceptable salt thereof.

The administration and dosage regimen of compounds of Formula I is considered to be done in the same manner as for the reference compound sumatriptan, cf: Oxford, GB 2,162,522A. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, intra-nasal, rectal and parenteral (i.e. intramuscular, intravenous and subcutaneous). Generally, it will be found that when a compound of the present invention is administered orally, a larger quantity of the active agent is required to produce the same effect as a smaller quantity given intranasally or parenterally. In accordance with good clinical practice, it is preferred to administer the instant compounds at a concentration level that will produce effective antimigraine effects without causing any harmful or untoward side effects.

The compounds of the present invention may be administered for antimigraine purposes either as individual therapeutic agents or as mixtures with other therapeutic agents. Therapeutically, they are generally given as pharmaceutical compositions comprised of an antimigraine amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and wetting agents (e.g. sodium lauryl sulfate). Solutions or suspensions of a Formula I compound with conventional pharmaceutical vehicles are employed for intra-nasal and parenteral compositions such as an aqueous solution for intravenous injection or an oily suspension for intramuscular injection.

The compounds of Formula I can be prepared by adaptation of the synthetic processes shown in Scheme A.

Processes for syntheses of some intermediate compounds are outlined in Scheme C. In addition, certain compounds and their syntheses will be set forth in more detail in the *Specific Embodiments* section, infra.

In the synthetic schemes, $R^1$ through $R^5$, X, m and n are as defined supra. The symbol Q represents a synthetic organic leaving group moiety such as tosyl, mesyl, halide, sulfate, phosphate, and so forth. Tosylate is also denoted Ts when it is the specified moiety. The symbol i-Pr denotes isopropyl and TIPS refers to the triisopropylsilyl group (-Si(i-Pr)$_3$).

Scheme A sets out the processes for synthesizing compounds of Formula I. The processes proceed either via a 5-amino-substituted intermediates of formulas (2 and 6). Selection of the preferred synthetic route mainly depends on the nature of the desired X-substituent on the squarate moiety.

Scheme B deals with synthetic pathways for intermediate compounds.

The reactions employed in Schemes A and B and their applications are familiar to the practitioner skilled in organic synthesis and modifications of conditions and reagents would be readily understood. The skilled synthetic chemist would know how to adapt these processes for preparation of specific Formula I compounds including other compounds embraced by this invention but not specifically disclosed. Variations of the methods to produce the same compounds in somewhat different fashion will also be evident to one skilled in the art. To provide greater detail in description, representative synthetic examples are provided infra in the "Specific Embodiments" section.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonance (NMR) spectral characteristics refer to chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as broad singlet (bs), singlet (s), multiplet (m), heptet (hept), quartet (q), triplet (t) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed either neat or using potassium bromide (KBr) as diluent. The elemental analyses are reported as percent by weight.

The following examples describe in detail the preparation of compounds of Formula I, as well as certain synthetic intermediates. It will be apparent to those skilled in the art that modifications, both of materials and methods, will allow preparation of other compounds disclosed herein. From the foregoing description and the following examples it is believed that one skilled in the art is able to use the invention to the fullest extent.

A. Preparation of Intermediate Compounds

Some representative procedures for preparation of synthetic intermediate compounds contained in the processes of the schemes are given hereinbelow. Most starting materials and certain intermediates are either commercially available or procedures for their synthesis are readily available in the chemical literature allowing their full utilization by one skilled in the art of organic synthetic chemistry.

EXAMPLE 1

5-[(5-Nitro-1H-indol-3-yl)methyl]-2,2-dimethyl-1,3-dioxane-4,6-dione (10)

An adaption of the procedure of Flaugh[1] was used. Thus, a solution of 5-nitroindole (50.0 g, 0.32 mol), Meldrum's acid (46.0 g, 0.32 mol), 37% aqueous formaldehyde (26.0 mL, 0.32 mol) and proline (1.8 g, 0.016 mol) in 200 mL of acetonitrile was stirred at room temperature for 18 h. The resulting thick yellow slurry was filtered and the filtercake was washed with acetonitrile, then acetone and finally with ether. This material was dried in vacuo to give the title compound (80.0 g, 81%) as a bright yellow solid, mp 182° C. (dec). The mother liquor was concentrated and then diluted with H$_2$O, and the resulting solid was collected, washed and dried as before to give a second crop of the product (7.0 g) as a darker yellow solid.

Total yield=87.0 g (89%): IR (KBr) 3330, 1767, 1732 cm$^{-1}$; $^1$H NMR (DMSO-d$_6$, 200 MHz) $\delta$11.64 (s, 1H), 8.63 (d, J=2.2 Hz, 1H), 7.96 (dd, J=9.0, 2.2 Hz, 1H), 7.49 (d, J=9.0 Hz, 1H), 7.33 (d, J=2.2 Hz, 1H), 4.84 (t, J=4.6 Hz, 1H), 3.45 (d, J=4.5 Hz, 2H), 1.78 (s, 3H), 1.55 (s, 3H). Anal. Calcd for C$_{15}$H$_{14}$N$_2$O$_6$: C, 56.60; H, 4.43; N, 8.80. Found: C, 56.62; H, 4.41; N, 8.91.

1. D. S. Farlow, M. E. Flaugh, S. D. Horvath, E. R. Lavignino, P. Pranc, Org. Prep. Proc. Int. 1981, 13, 39.

EXAMPLE 2

Ethyl 5-nitro-3-(1H-indole)propionate

To a solution of [5-(5-nitroindol-3-yl)methyl]-2,2-dimethyl-1,3-dioxane-4,6-dione (10.0 g, 0.031 mol) in a mixture of pyridine (80 mL) and absolute ethanol (20 mL) was added 0.1 g of copper powder and the mixture was heated to reflux under Ar for 2 h. The cooled mixture was filtered and the filtrate was evaporated. The resulting residue was triturated with etherdichloromethane to give the title compound (7.3 g, 89%) as a solid, mp 118°–121° C.: IR (KBr) 3330, 1730 cm$^{-1}$; $^1$H NMR (DMSO-d$_6$, 200 MHz) δ11.59 (br s, 1H), 8.53 (d, J=2.2 Hz, 1H), 7.97 (dd, J=9.0, 2.3 Hz, 1H), 7.49 (d, J=9.0 Hz, 1H), 7.40 (d, J=2.1 Hz, 1H), 4.03 (q, J=7.1 Hz, 2H), 3.02 (t, J=7.4 Hz, 2H), 2.67 (t, J=7.4 Hz, 2H), 1.13 (t, J=7.1 Hz, 3H).

EXAMPLE 3

5-Nitro-3-(3-hydroxypropyl)-1H-indole (5)

To a suspension of 95% LiAlH$_4$ (2.20 g, 0.058 mol) in 60 mL of dry THF was added a solution of ethyl 5-nitro-3indolepropionate (7.30 g, 0.028 mol) in 100 mL of dry THF, at 0° C. under Ar. After stirring for 20 min, the mixture was quenched by the cautious addition of 3 mL of H$_2$O. The resulting suspension was stirred for 10 min and then it was filtered and the filtercake was washed with additional THF. The filtrate was evaporated and the residue was taken up in ether, dried (Na$_2$SO$_4$) and evaporated, and the resulting solid was triturated with hexane to give the title compound (4.30 g, 70%) as a yellow solid, mp 107°–110° C.: IR (KBr) 3480, 3180, 1625 cm$^{-1}$; $^1$H NMR (CDCl$_3$, 200 MHz) δ6 8.60 (d, J=2.1 Hz, 1H), 8.35 (br s, 1H), 8.11 (dd, J=9.0, 2.2 Hz, 1H), 7.38 (d, J=8.9 Hz, 1H), 7.16 (m, 1H), 3.75 (t, J=6.2 Hz, 2H), 2.91 (t, J=7.2 Hz, 2H), 2.07-1.93 (m, 2H), 1.37 (br s, 1H).

EXAMPLE 4a

3-(3-Bromopropyl)-5-nitro-1H-indole (4)

To a solution of triphenylphosphine (6.70 g, 0.025 mol) in 80 mL of acetonitrile was added a solution of 5-nitro-3-(3-hydroxypropyl)indole (4.30 g, 0.020 mol) in 75 mL of acetonitrile, followed by a solution of CBr$_4$ (9.00 g, 0.027 mol) in 25 mL of acetonitrile, at 0° C. under Ar. The mixture was stirred at room temperature for 3 h and then it was evaporated and the residue was chromatographed (SiO$_2$/ethyl acetate-hexane, 1:9 then 1:4) to give the title compound (4.60 g, 84%) as a solid, mp 92°–95° C.: IR (neat) 3420, 1330 cm$^{-1}$; $^1$H NMR (CDCl$_3$, 200 MHz) δ8.59 (d, J=2.1 Hz, 1H), 8.40 (br s, 1H), 8.13 (dd, J=9.0, 2.2 Hz, 1H), 7.40 (d, J=9.1 Hz), 1H), 7.21 (d, J=2.2 Hz, 1H), 3.45 (t, J=6.4 Hz, 2H), 2.99 (t, J=7.2 Hz, 2H), 2.26 (m, 2H).

EXAMPLE 4b

3-[3-Iodopropyl]-5-nitro-1H-indole. (4)

A solution of 3-[3-hydroxypropyl]-5-nitro-1H-indole (1.13 g, 5.06 mmol) in 20 mL of acetonitrile was cooled to 0° C. and treated sequentially with triethylamine (1.05 mL, 7.59 mmol) and methanesulfonyl chloride (0.43 mL, 5.6 mmoL) and the mixture stirred for 30 min. The reaction mixture was quenched with 30 mL of water and the organic material was extracted into ethyl acetate. The organic extracts were dried (MgSO$_4$) and concentrated in vacuo. The crude residue was dissolved in 20 mL of acetonitrile containing KI (1.7 g, 10.1 mmol) and heated to reflux for 3 h. The reaction mixture was cooled and the solvent removed in vacuo. The residue was dissolved in 100 mL of ethyl acetate and washed with water. The ethyl acetate layer was dried (MgSO$_4$) and concentrated and the residue was purified by flash column chromatography (20% ethyl acetate in hexanes) to give the title compound 1.37 g, 4.20 mmol, 83%) as a yellow solid: mp 95°–98° C.; $^1$H NMR (DMSO-d$_6$, 300 MHz) δ8.53 (d, J=2.3 Hz, 1H), 7.97 (dd, J=2.3, 9.0 Hz, 1H), 7.51 (d, J=9.0 Hz, 1H) 7.43 (s, 1H), 3.30 (t, J=6.7 Hz, 2H), 2.84 (t, J=7.7 Hz, 2H), 2.11 (m, 2H); IR (KBr) 1330, 1510, 810 cm$^{-1}$; MS (m/e) 330 (M+) . Anal. Calcd for C$_{11}$H$_{11}$IN$_2$O$_2$: C, 40.02, H 3.36, N 8.48. Found: C, 40.26; H, 3.27; N, 8.51.

EXAMPLE 5

5-Bromo-3-(3-hydroxypropyl)-1H-indole (11)

A modification of a procedure reported by Grandberg (Chem. Abstr. 1973, 79,918895) was used. Thus, to a suspension of 4-bromophenylhydrazine hydrochloride (56.0 g, 0.25 mol) in 200 mL of 2-methoxyethanol was added 3,4-dihydro-2H-pyran (25.5 mL, 0.28 mol) over ca. 5 min and the resulting mixture was heated to reflux under Ar for 3.5 h. The cooled reaction mixture was evaporated and the residual oil was poured into 500 mL of cold water. The aqueous mixture was extracted with ether (2×250 mL) and the ethereal extract was washed with H$_2$O (250 mL), 1N HCl (2×250 mL) and brine (250 mL). The organic phase was then dried (Na$_2$SO4) and evaporated to give a dark orange-brown oil. This oil was purified on a 10×15 cm SiO$_2$ pad (elution with CH$_2$Cl$_2$ then CH$_2$Cl$_2$-ethyl acetate, 1:1) to give the title compound (43.7 g, 69%) as a viscous orange-brown oil: IR (neat) 3570, 3430, 3300 (br), 1460 cm$^{-1}$; $^1$H NMR (CDCl$_3$, 200 MHz) δ0.11 (br s, 1H), 7.73 (d, J=1.8 Hz, 1H), 7.30-7.18 (m, 2H), 6.97 (s, 1H), 3.72 (t, J=6.4 Hz, 2H), 2.80 (t, J=7.5 Hz, 2H), 2.03-1.89 (m, 2H), 1.68 (br s, 1H).

EXAMPLE 6

5-Aminomethyl-3-(3-hydroxypropyl)indole (6)

To a solution of 5-cyano-3-(3-hydroxypropyl)indole (1.00 g, 0.005 mol) in 30 mL of absolute ethanol was added 10% palladium-on-charcoal (1.00 g) and the mixture was hydrogenated on a Parr shaker at 40 psi for 6 h. The mixture was then filtered, through Celite, the filtercake was washed with additional ethanol and the filtrate was evaporated to give a colourless gum. Flash chromatography (SiO$_2$/MeCN-MeOH, 9:1 then MeCN-MeOH-NH$_4$OH, 90:9:1) afforded the essentially pure title compound (0.67 g, 70%) as a colourless gum: IR (neat) 3250 cm$^{-1}$; $^1$H NMR (DMSO-d$_6$, 200 MHz) δ10.60 (s, 1H) , 7.41 (s, 1H), 7.23 (d, J=8.2 Hz, 1H), 7.04 (s, 1H), 7.02 (d, J=8.1 Hz, 1H), 4.4 (br s, 1H), 3.75 (s, 2H), 3.46 (t, J=6.5 Hz, 2H), 3.3 (br s, 2H), 2.68 (m, 2H), 1.78 (m, 2H).

EXAMPLE 7

5-(1,2-Dioxo-4-methyl-3-cyclobuten-3-yl)aminomethyl-3-(3-3-hydroxypropyl)indole (8a)

To a solution of 5-aminomethyl-3-(3-hydroxypropyl)indole (0.65 g, 0.0032 mol) in 12 mL of absolute ethanol was added 3-(1-methylethoxy)-4-methylcyclobut-3-ene-1,2-dione $^2$(0.56 g, 0.0036 mol) and the mixture was stirred at room temperature under Ar for 20 h. Evaporation of the resulting mixture gave a brown gum which was chromatographed (SiO$_2$/CH$_2$Cl$_2$ the CH$_2$Cl$_2$-MeOH, 95:5) to give the title compound (0.49 g, 51%) as an off-white foam: IR (neat) 3300 (br), 1785, 1720, 1600 (br) cm$^{-1}$; $^1$H NMR (DMSO-d$_6$, 200 MHz) δ10.75 (s, 1H), 9.45 (m, 0.3H), 9.18 (m, 0.7H), 7.44 (S, 1H), 7.33 (d, J=8.4 Hz, 1H), 7.10 (s, 1H), 6.98 (d, J=8.4 Hz, 1H), 4.77 (s, 1H), 4.61 (m, 1H), 4.42 (m, 1H), 3.43 (m, 2H), 2.68 (m, 2H), 2.14 (s, 1.2H), 2.05 (s, 1.8H), 1.77 (m, 2H).

EXAMPLE 8

5-(1,2-Dioxo-4-methyl-3-cyclobuten-3-yl)aminomethyl-3-(3-methanesulfonyloxypropyl)indole (9)

To a solution of 5-(1,2-dioxo-4-methyl-3-cyclobuten-3-yl)aminomethyl-3-(3-hydroxypropyl)indole (0.48 g, 0.0016 mol) in 45 mL of dichloromethane-THF (4:1), cooled at −20° C. under Ar, was added triethylamine (0.28 mL, 0.002 mol) followed by methanesulfonyl chloride (0.16 mL, 0.002 mol). The resulting solution was stirred at −20° C. for 1.5 h and then it was washed (brine), dried (Na$_2$SO$_4$) and evaporated to give a brown gum. This material was chromatographed (SiO$_2$/ethyl acetate) to give the title compound (0.50 g, 83%) as a beige foam: IR (neat) 3320 (br), 1785, 1727, 1600 (br), 1350 (br) cm$^{-1}$; $^1$H NMR (DMSO-d$_6$, 200 MHz) δ10.86 (s, 1H), 9.45 (m, 0.5H), 9.21 (m, 0.5H), 7.48 (s, 1H), 7.33 (d, J=8.3 Hz, 1H), 7.17 (s, 1H), 7.03 (d, J=8.3 Hz, 1H), 4.78 (d, J=5.9 Hz, 1.2H), 4.62 (d, J=6.0 Hz, 0.8H), 4.23 (m, 2H), 3.80 (s, 3H), 3.06 (m, 2H), 2.76 (m, 2H), 2.14 (s, 1.2H), 2.05 (s, 1.8H).

EXAMPLE 9

2-Iodo-4-nitroaniline (12)

To a solution of 4-nitroaniline (27.6 g, 0.2 mol) in 200 mL of dry acetonitrile was added a solution of ICl (31.0 g, 0.19 mol) in 50 mL of acetonitrile and the mixture was stirred at room temperature for 18 h. The reaction mixture was then poured into ethyl acetate, washed (20% aq. Na$_2$S$_2$O$_3$, brine), dried (Na$_2$SO$_4$) and evaporated to give a brown solid. Chromatography (SiO$_2$/CH$_2$Cl$_2$-hexane, 6:4 to 7:3) afforded the title compound (18.0 g, 36%) as a yellow solid, mp 104°–106° C.: IR (neat) 3480, 3380, 1610, 1300 cm$^{-1}$; $^1$H NMR (DMSO-d$_6$, 200 MHz) δ8.38 (d, J=2.6 Hz, 1H), 7.97 (dd, J=9.0, 2.6 Hz, 1H), 6.75 (d, J=9.0 Hz, 1H), 6.73 (s, 2H).

EXAMPLE 10

1-(Trimethylsilyl)-4-(t-butyldimethylsiloxy)-1-butyne (13)

To a solution of 3-butyne-1-ol (21.0 g, 0.3 mol) in 100 mL of DMF was added imidazole (41.3 g, 0.6 mol), followed by a solution of t-butyldimethylsilyl chloride (48.0 g, 0.32 mol) in 25 mL of DMF. After stirring at room temperature under Ar for 18 h, the reaction mixture was poured into 10% aqueous NaHCO$_3$ (150 mL) and extracted with hexane (3×250 mL). The organic phase was washed (brine), dried (Na$_2$SO$_4$) and evaporated to give 1-(t-butyl dimethylsiloxy)-3-butyne (49.0 g, 89%) as a colourless oil: IR (neat) 3320, 2125 (w), 1260, 1110, 840 cm$^{-1}$; $^1$H NMR (CDCl$_3$, 200 MHz) δ3.74 (t, J=7.2 Hz, 2H), 2.40 (dt, J=7.1, 2.6 Hz, 2H), 1.96 (t, J=2.6 Hz, 1H), 0.90 (s, 9H), 0.07 (s, 6H).

To a solution of 1-(t-butyldimethylsiloxy)-3-butyne (49.0 g, 0.27 mol) in 250 mL of THF, at −78° C. under Ar, was added a solution of n-butyllithium (1.6 M in hexane, 170 mL, 0.27 mol) over ca. 45 min. The mixture was stirred at −78° C. for 30 min and then at 0° C. for 1.5 h. The resulting solution was recooled at −78° C. and then trimethylsilyl chloride (34.0 mL, 0.27 mol) was added dropwise. After the addition the mixture was allowed to warm to room temperature over 18 h and then it was diluted with hexane, washed (H$_2$O, sat. aq. NaHCO$_3$, brine), dried (Na$_2$SO$_4$) and evaporated to give an oil. Distillation at reduced pressure afforded the title compound (60.0 g, 88%) as a colourless oil, bp 70°–75° C./0.1 mm: IR (neat) 2180, 1253, 1112, 841 cm$^{-1}$; $^1$H NMR (CDCl$_3$, 200 MHz) δ3.72 (t, J=7.0 Hz, 2H), 2.43 (t, J=7.0 Hz, 2H), 0.90 (s, 9H), 0.14 (s, 9H), 0.07 (s, 6H).

EXAMPLE 11

5-Nitro-2-trimethylsilyl-3-(2-t-butyldimethylsiloxyethyl)indole (14)

A mixture of 2-iodo-4-nitroaniline (7.92 g, 0.030 mol), 1-(trimethylsilyl)-4-(t-butyldimethylsiloxy)-1-butyne (15.36 g, 0.060 mol), potassium acetate (14.70 g, 0.15 mol), lithium chloride (1.27 g, 0.030 mol) and palladium (II) acetate (0.675 g, 0.003 mol) in 100 mL of dry DMF was heated at 70° C. (oil-bath temperature) under Ar for 2.5 h. The cooled reaction mixture was diluted with ether and the aqueous phase was separated and extracted with ethyl acetate. The combined organic phases were washed (H$_2$O, brine), dried (Na$_2$SO$_4$) and evaporated. The resulting residue was chromatographed (SiO$_2$/hexane-ethyl acetate, 4:1) to give a dark orange solid which was rechromatographed (SiO$_2$/hexane-CH$_2$Cl$_2$, 4:1 to 6:4) to give the title compound (5.00 g, 42%) as a yellow solid: IR (neat) 3414, 1328, 1253, 845 cm$^{-1}$; $^1$H NMR (CDCl$_3$, 200 MHz) δ8.63 (d, J=2.2 Hz, 1H), 8.21 (br s, 1H), 8.09 (dd, J=9.0, 2.2 Hz, 1H), 7.35 (d, J=9.0 Hz, 1H), 3.84 (t, J=7.2 Hz, 2H), 3.09 (t, J=7.2 Hz, 2H), 0.85 (s, 9H), 0.42 (s, 9H), −0.01 (s, 6H).

EXAMPLE 12

5-Nitro-3-(2-hydroxyethyl)indole (5)

To a solution of 5-nitro-2-trimethylsilyl-3-(2-t-butyldimethylsiloxyethyl)indole (7.30 g, 0.019 mol) in 125 mL of acetonitrile was added 48% HF (3.0 mL, 0.084 mol) and the mixture was stirred at room temperature for 1 h. Another 2.5 mL (0.07 mol) of 48% HF was added and stirring was continued for 18 h. The mixture was then cautiously basified with saturated aqueous Na$_2$CO$_3$ and extracted with ethyl acetate. The organic extract was washed (brine), dried (Na$_2$SO$_4$) and evaporated to give a gum. This material was triturated with ether and the supernatant was evaporated to give a gum. Chromatography (SiO$_2$/hexane-ethyl acetate, 1:1) of this gum gave the title compound (2.24 g, 57%) as a solid, mp 90° C.: IR (neat) 3380 (br), 1622, 1330 cm$^{-1}$; $^1$H NMR (CDCl$_3$, 200 MHz) δ8.60 (d, J=1.7 Hz, 1H), 8.48 (br s, 1H), 8.12 (dd, J=9.0, 1.7 Hz, 1H), 7.40 (d, J=9.0 Hz, 1H), 3.96 (t, J=6.3 Hz, 2H), 3.07 (t, J=6.3 Hz, 2H), 1.56 (s, 1H).

EXAMPLE 13

5-Nitro-3-(2-bromoethyl)indole (4)

To a solution of triphenylphosphine (2.83 g, 0.011 mol) in 100 mL of acetonitrile was added a solution of 5-nitro-3-(2-hydroxyethyl)indole (2.00 g, 0.0097 mol) in 25 mL of acetonitrile, followed by a solution of CBr$_4$ (3.60 g, 0.011 mol) in 25 mL of acetonitrile, at 0° C. under Ar. The mixture was stirred at room temperature for 18 h and then another 0.283 g (1.1 mmol) of triphenylphosphine and 0.360 g (1.1 mmol) of CBr$_4$ were added. After 2.5 h the mixture was diluted with ethyl acetate, washed (H$_2$O, brine), dried (Na$_2$SO$_4$) and evaporated and the residue was chromatographed (SiO$_2$./ethyl acetate-hexane, 1:4) to give the title compound (2.27 g, 87%) as a yellow solid: IR (neat) 3370, 1334 cm$^{-1}$; $^1$H NMR (DMSO-d$_6$, 200 MHz) δ11.69 (s, 1H), 8.60 (d, J=2.1 Hz, 1H), 7.98 (dd, J=9.0, 2.2 Hz, 1H), 7.54-7.49 (m, 2H), 3.76 (t, J=7.2 Hz, 2H), 3.32 (t, J=7.2 Hz, 2H).

EXAMPLE 14

5-Nitro-3-[2-(dimethylamino)ethyl]indole (3)

Into 50 mL of absolute ethanol cooled at 0° C. was bubbled dimethylamine for 30 min. To this solution was added a solution of 5-nitro-3-(2-bromoethyl)indole (0.50 g, 1.86 mmol) in 50 mL of absolute ethanol and the mixture was transferred to a pressure vessel and heated at 80° C. for 2 h. The cooled mixture was then evaporated and the residue was partitioned between 1N NaOH and ethyl acetate. The organic phase was separated, washed (brine), dried (Na$_2$SO$_4$) and evaporated to give the title compound (0.40 g, 92%) as a yellow solid, mp 132°-135° C.: IR (neat) 1330 cm$^{-1}$; $^1$H NMR (CDCl$_3$, 200 MHz) δ9.23 (s, 1H), 8.54 (s, 1H), 7.98 (d, J=8.8 Hz, 1H), 7.26-7.10 (m, 2H), 2.98 (m, 2H), 2.71 (m, 2H), 2.37 (s, 6H).

EXAMPLE 15

5-Amino-3-[2-(dimethylamino)ethyl]indole (2)

A mixture of 5-nitro-3-[2-(dimethylamino) ethyl]indole (0.650 g, 2.79 mmol) and 10% palladium-on-charcoal (0.150 g) in 60 mL of ethanol was hydrogenated on a Parr shaker at 40 psi for 30 min. The mixture was then filtered through Celite and the catalyst was washed with additional ethanol. Evaporation of the filtrate gave the essentially pure title compound (0.510 g, 90%) as a light brown gum: IR (neat) 3410, 1630, 1588, 1464 cm$^{-1}$; $^1$H NMR (CDCl$_3$, 200 MHz) δ7.84 (br s, 1H), 7.15 (d, J=8.5 Hz, 1H), 6.94 (d, J=2.2 Hz, 1H), 6.90 (d, J=2.1 Hz, 1H), 6.66 (dd, J=8.5, 2.2 Hz, 1H), 3.44 (br s, 2H), 2.88 (m, 2H), 2.60 (m, 2H), 2.34 (s, 6H).

B. Preparation of Formula I Compounds

In general, Formula I compounds can be readily prepared by reaction of formula (2) intermediates with appropriate cyclobutene diones or by reacting formula (8b) or (9) compounds with appropriate secondary amines.

EXAMPLE 16

5-(1,2-Dioxo-4-methyl-3-cyclobuten-3-yl)-amino-3-[2-dimethylamino)ethyl]indole

A solution of 5-amino-3-[2-(dimethylamino)ethyl]indole (0.250 g, 1.23 mmol) and 3-(1-methylethoxy)-4-methylcyclobut-3-ene-1,2-dione[2] (0.200 g, 1.30 mmol) in 8 mL of absolute ethanol was stirred at room temperature under Ar for 24 h. Evaporation of the resulting mixture gave a gum which was chromatographed (SiO$_2$/CH$_2$Cl$_2$-MeOH, 95:5 then CH$_2$Cl$_2$-MeOH-NH$_4$ OH, 95:4.5:0.5 to 90:9:1) to give the title compound (0.200 g, methanolic HCl and the solution was concentrated. The resulting solid was filtered, washed with ether and dried in vacuo to give the hydrochloride (0.180g) as a pale yellow solid, mp 135°-140° C.: IR (K Br) 3330, 3260, 1781, 1711, 1598, 1577 cm$^{-1}$; $^1$H NMR (DMSO-d$_6$, 200 MHz) δ11.19 (s, 0.5H), 11.08 (s, 0.5H), 1095 (s, 0.5H), 10.86 (s, 0.5H), 7.61-7.02 (m, 4H), 3.33 (m, 2H), 3.08 (m, 2H), 2.84 (s, 6H), 2.26 (s, 1.6H), 1.90 (s, 1.4H). Anal. Calcd for C$_{17}$H$_{19}$N$_3$O$_2$. HCl. 1.2 H$_2$O: C, 57.44; H, 6.35; N, 11.82. Found: C, 57.24; H, 6.20; N, 11.75.

2. L. S. Liebeskind, R. W. Rengl, D. R. Wirtz, T. T. Shaw, J. Org. Chem. 1988, 53, 2482.

EXAMPLE 17

Alternatively, compounds of Formula 1 may be prepared as depicted in Sequence 2, Scheme A. For example the 3-(3-methanesulfonyloxypropyl)indole derivative 9, can be treated with an excess of an N,N-dialkylamine in a suitable solvent such as ethanol to afford compounds of type 1 where R$^4$=H. Coversion of intermediate 6 to 15 may be achieved by mono-N-alkylation employing the appropriate alkyl halide (R$^4$Q) in an aprotic solvent such as acetonitrile or dimethylformamide in the presence of an HCl scavenger such as potassium carbonate. Another possible route to 15 entails N-acylation of 6 with an acyl halide (R$^5$COQ) followed by reduction of the acylated intermediate with lithium aluminum hydride or diborane in ether or tetrahydrofuran. Reaction of 15 with a suitably-substituted cyclobutane-1,2-dione in ethanol would provide 8b which could then be converted to 9 (R$^4$=alkyl) via reaction with methanesulfonyl chloride. Displacement of the methanesulfonyloxy leaving group by an N,N-dialylamine would provide Formula 1 compounds in which R$^4$=alkyl.

EXAMPLE 18

Pharmacologic Studies in the Canine Lateral Saphenous Vein

The lateral saphenous vein is obtained from an anesthetized dog and trimmed of adherent material. The vessel is then cut into 2-3 mm ring segments and mounted between stainless steel wires in tissue baths containing 20mL of modified Kreb's buffer which is continuously aerated with 5% CO$_2$/95%O$_2$ and maintained at 37° C. Resting tension is manually adjusted to 1 gram and maintained until a stable baseline is achieved for an equilibration period of 1 h. Tissue bath solution is replaced every 15 min during this equilibration.

Ketanserin, atropine and pyrilamine are added to the baths at a concentration of 1 μM to block 5-HT$_2$, cholinergic and histaminic effects. After 15 min, with the antagonists in place, a serotonin concentration response curve is conducted in a cumulative fashion. At the conclusion the baths are washed out several times, tension is readjusted to 1 gram and the tissue is allowed to return to equilibrium over a period of 45-60 min. The antagonists are again added to the baths and after 15 min, concentration response curves are generated for selected test compounds. Individual vessel segments are only exposed to one test compound.

The activity of test compounds is expressed in terms of relative potency and efficacy compared with 5-HT (arbitrarily assigned a value of 1.0) in the same vascular preparation.

SCHEME A
Synthesis of Formula I Compounds

Sequence 1.

-continued
SCHEME A
Synthesis of Formula I Compounds
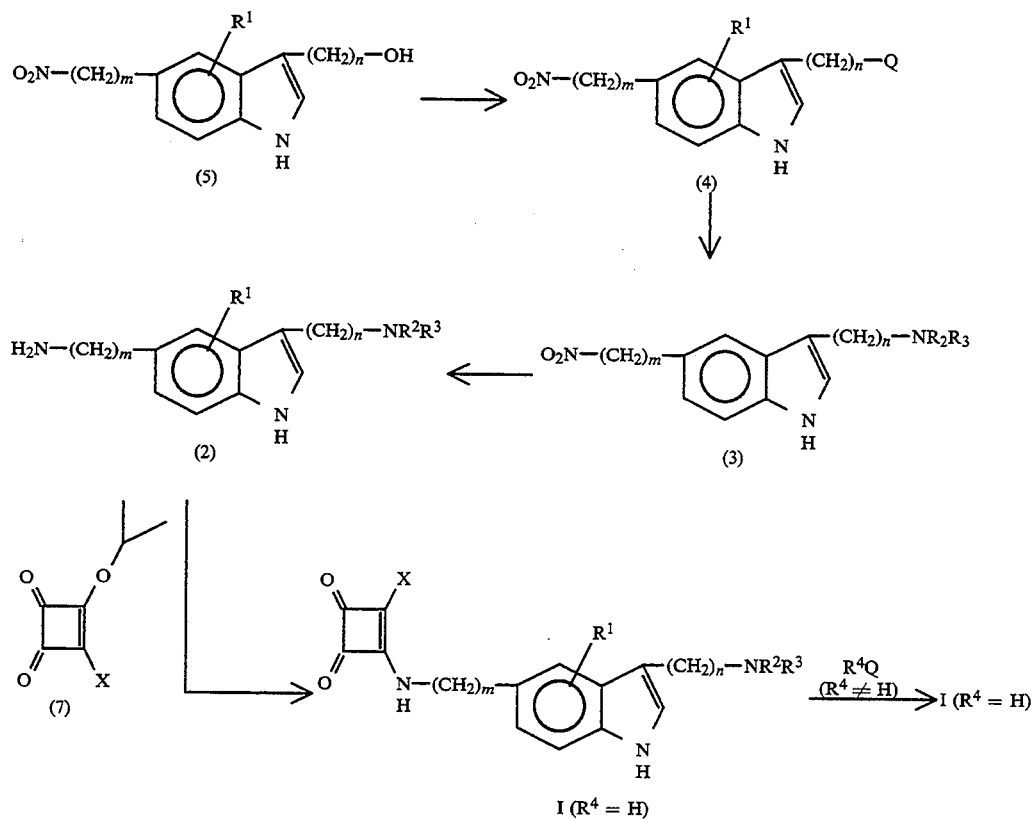
Sequence 2.
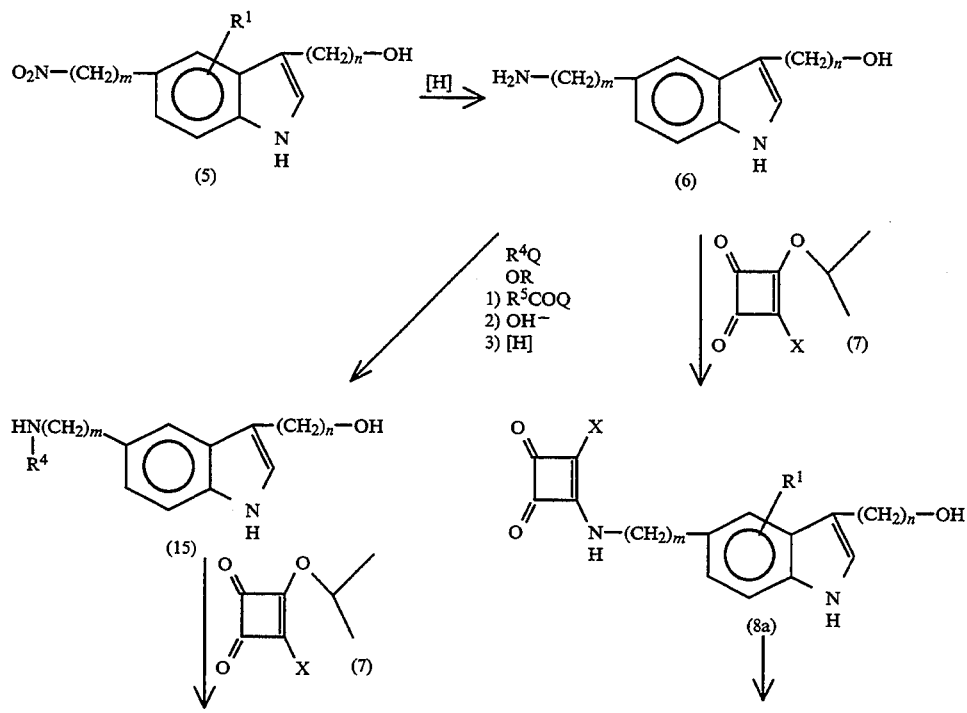

-continued
SCHEME A
Synthesis of Formula I Compounds
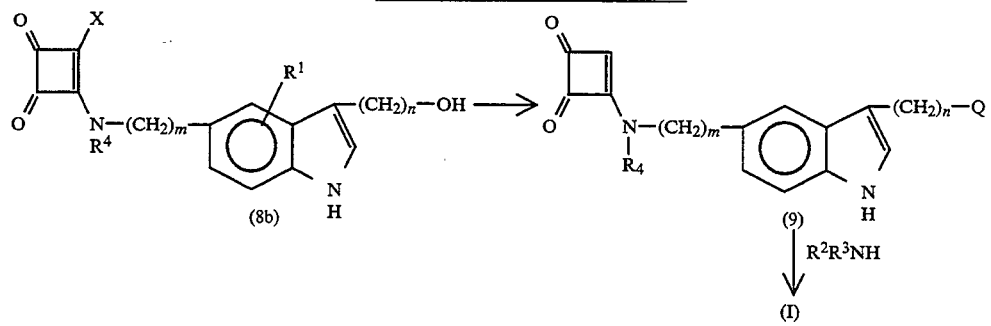
Scheme B Synthesis of Intermediate Compounds
The following synthetic reactions are intended to provide examples of some of the available methods of preparing chemical intermediate compounds for use in the process of Scheme A.
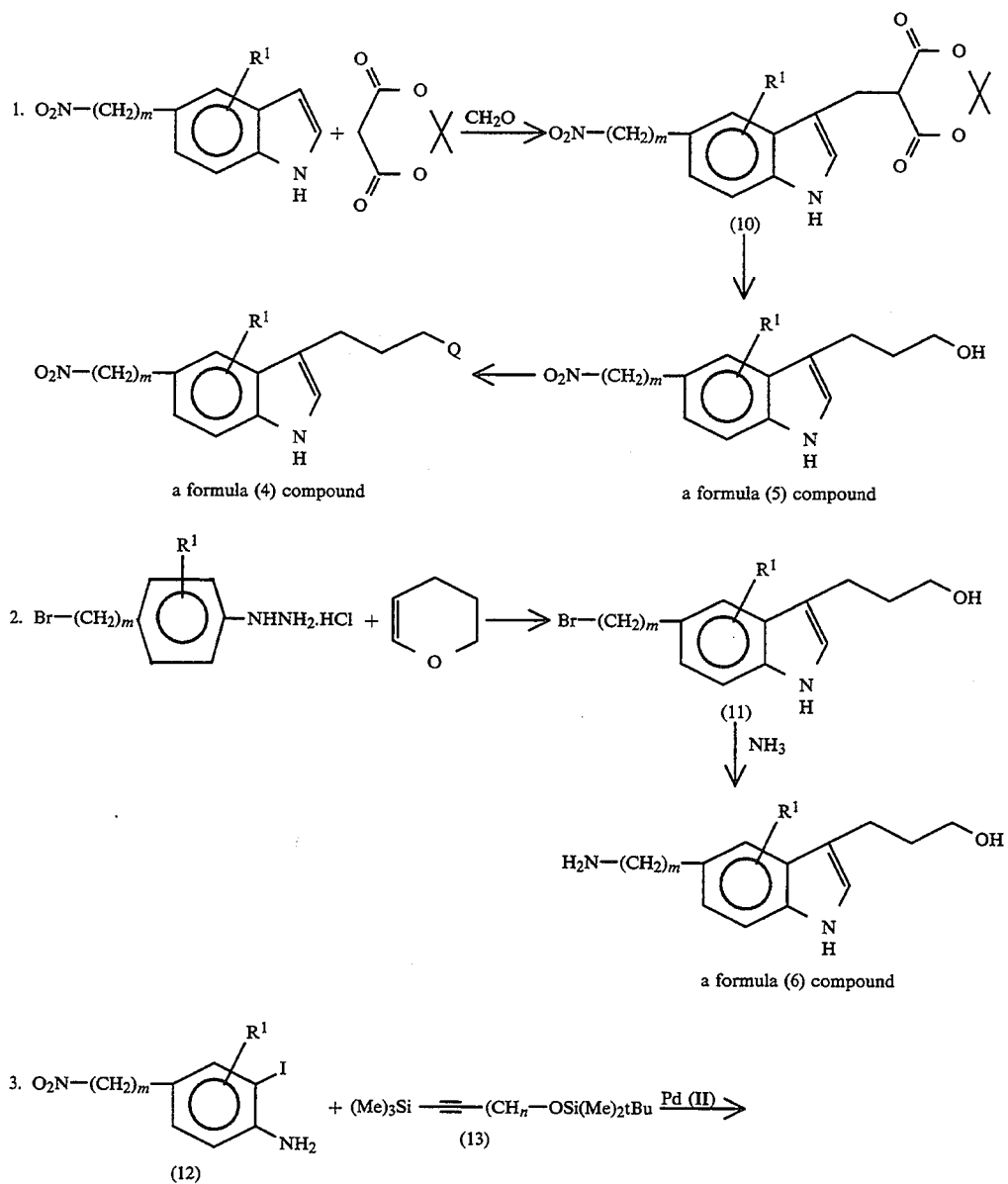

-continued

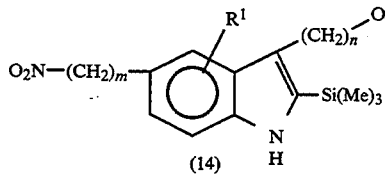

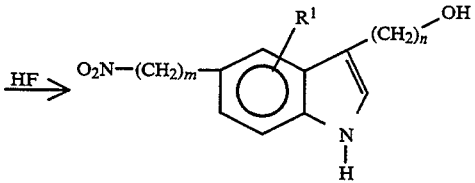

a Formula (5) compound

We claim:

1. A compound of Formula I or a pharmaceutically acceptable acid addition salt and/or solvate thereof

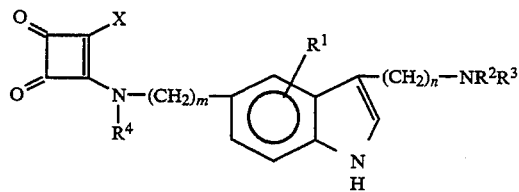

wherein $R^1$ is selected from hydrogen, halogen and lower alkyl;

$R^2$ and $R^3$ are independently selected from hydrogen and lower alkyl;

$R^4$ is selected from hydrogen, lower alkyl, lower acyl and lower alkylsulfonyl;

X is selected from $-NR^2R^3$, $-OR^2$, and $R^6$, wherein $R^6$ can be hydrogen, lower alkyl, cycloalkyl, phenyl, and phenyl-lower alkyl;

m is selected from zero and the integers 1 to 3; and n is selected from the integers 1 to 5.

2. The compound of claim 1 wherein m is zero and n is 2.

3. The compound of claim 1, 5-(1,2-Dioxo-4-methyl-3-cyclobuten-3-yl)amino-3-[2-(dimethylamino) ethyl]indole.

4. The method for treating vascular headaches by administering a therapeutically effective amount of a compound claimed in claim 1 to a person suffering from a vascular headache.

5. A method for preventing vascular headache by administering a prophylactically effective amount of a compound claimed in claim 1 to a person suffering the onset of a vascular headache.

6. A pharmaceutical composition in unit dosage form suitable for systemic administration to a person at risk of or suffering a vascular headache, the composition comprising a pharmaceutical carrier and from about 1 to 500 mg of a compound claimed in claim 1.

* * * * *